US009020593B2

(12) United States Patent
Arcot-Krishnamurthy et al.

(10) Patent No.: US 9,020,593 B2
(45) Date of Patent: Apr. 28, 2015

(54) SELECTION OF PACING SITES TO ENHANCE CARDIAC PERFORMANCE

(71) Applicant: Cardiac Pacemakers, Inc., St. Paul, MN (US)

(72) Inventors: Shantha Arcot-Krishnamurthy, Renton, WA (US); Michael J. Stucky, Shoreview, MN (US); Yinghong Yu, Shoreview, MN (US); Jiang Ding, Shoreview, MN (US)

(73) Assignee: Cardiac Paemakers, Inc., St. Paul, MN (US)

( * ) Notice: Subject to any disclaimer, the term of this patent is extended or adjusted under 35 U.S.C. 154(b) by 0 days.

(21) Appl. No.: 14/087,826

(22) Filed: Nov. 22, 2013

(65) Prior Publication Data
US 2014/0067002 A1   Mar. 6, 2014

Related U.S. Application Data

(63) Continuation of application No. 11/479,877, filed on Jun. 30, 2006, now Pat. No. 8,620,430.

(51) Int. Cl.
*A61N 1/362* (2006.01)
*A61N 1/365* (2006.01)

(52) U.S. Cl.
CPC ........ *A61N 1/36585* (2013.01); *A61N 1/36514* (2013.01); *A61N 1/36535* (2013.01); *A61N 1/36542* (2013.01); *A61N 1/36557* (2013.01); *A61N 1/36578* (2013.01); *A61N 1/36592* (2013.01)

(58) Field of Classification Search
USPC ................ 607/9, 11, 17–19, 23, 27
See application file for complete search history.

(56) References Cited

U.S. PATENT DOCUMENTS

| 5,417,717 | A | 5/1995 | Salo et al. |
| 6,021,351 | A | 2/2000 | Kadhiresan et al. |
| 6,044,298 | A | 3/2000 | Salo et al. |
| 6,221,011 | B1 | 4/2001 | Bardy |
| 6,270,457 | B1 | 8/2001 | Bardy |
| 6,277,072 | B1 | 8/2001 | Bardy |
| 6,280,380 | B1 | 8/2001 | Bardy |

(Continued)

FOREIGN PATENT DOCUMENTS

| JP | 2005538776 | 12/2005 |
| WO | 2006039693 A1 | 4/2006 |

OTHER PUBLICATIONS

Office Action from U.S. Appl. No. 11/601,216 dated Jul. 13, 2009, 16 pages.

(Continued)

*Primary Examiner* — Rex R Holmes
(74) *Attorney, Agent, or Firm* — Seager, Tufte & Wickhem, LLC

(57) ABSTRACT

Systems and methods for selection of electrodes and related pacing configuration parameters used to pace a heart chamber are described. A change in the hemodynamic state of a patient is detected. Responsive to the detected change, a distribution of an electrical, mechanical, or electromechanical parameter related to contractile function of a heart chamber with respect to locations of multiple electrodes disposed within the heart chamber is determined. A pacing output configuration, including one or more electrodes of the multiple electrodes, is selected and the heart chamber is paced using the selected pacing output configuration.

20 Claims, 5 Drawing Sheets

(56) References Cited

U.S. PATENT DOCUMENTS

| | | | |
|---|---|---|---|
| 6,285,906 B1 | 9/2001 | Ben-Haim et al. | |
| 6,312,378 B1 | 11/2001 | Bardy | |
| 6,336,903 B1 | 1/2002 | Bardy | |
| 6,358,203 B2 | 3/2002 | Bardy | |
| 6,368,284 B1 | 4/2002 | Bardy | |
| 6,398,728 B1 | 6/2002 | Bardy | |
| 6,440,066 B1 | 8/2002 | Bardy | |
| 6,473,645 B1 | 10/2002 | Levine | |
| 6,567,700 B1 * | 5/2003 | Turcott et al. | 607/9 |
| 6,606,516 B2 | 8/2003 | Levine | |
| 6,708,061 B2 | 3/2004 | Salo et al. | |
| 6,795,732 B2 | 9/2004 | Stadler et al. | |
| 6,832,112 B1 | 12/2004 | Bornzin | |
| 6,876,881 B2 | 4/2005 | Baumann et al. | |
| 6,909,916 B2 | 6/2005 | Spinelli et al. | |
| 6,915,160 B2 | 7/2005 | Auricchio et al. | |
| 6,965,797 B2 * | 11/2005 | Pastore et al. | 607/17 |
| 6,973,349 B2 | 12/2005 | Salo | |
| 6,980,851 B2 | 12/2005 | Zhu et al. | |
| 6,999,815 B2 | 2/2006 | Ding et al. | |
| 7,010,347 B2 | 3/2006 | Schecter | |
| 7,013,176 B2 | 3/2006 | Ding et al. | |
| 7,041,061 B2 | 5/2006 | Kramer et al. | |
| 7,113,823 B2 | 9/2006 | Yonce et al. | |
| 7,177,688 B2 | 2/2007 | Salo et al. | |
| 7,181,284 B2 | 2/2007 | Burnes et al. | |
| 7,209,786 B2 | 4/2007 | Brockway et al. | |
| 7,239,913 B2 | 7/2007 | Ding et al. | |
| 7,257,443 B2 | 8/2007 | Pastore et al. | |
| 7,292,887 B2 | 11/2007 | Salo et al. | |
| 7,310,554 B2 | 12/2007 | Kramer et al. | |
| 7,319,900 B2 | 1/2008 | Kim et al. | |
| 7,346,394 B2 | 3/2008 | Liu et al. | |
| 2001/0003159 A1 | 6/2001 | Dooley et al. | |
| 2002/0007198 A1 | 1/2002 | Haupert et al. | |
| 2002/0151934 A1 | 10/2002 | Levine | |
| 2003/0078624 A1 | 4/2003 | Carlson et al. | |
| 2003/0078630 A1 | 4/2003 | Lovett et al. | |
| 2003/0120316 A1 | 6/2003 | Spinelli et al. | |
| 2004/0015081 A1 | 1/2004 | Kramer et al. | |
| 2004/0030357 A1 | 2/2004 | Salo et al. | |
| 2004/0054381 A1 | 3/2004 | Pastore et al. | |
| 2004/0098056 A1 | 5/2004 | Ding et al. | |
| 2004/0102812 A1 | 5/2004 | Yonce et al. | |
| 2004/0193223 A1 * | 9/2004 | Kramer et al. | 607/9 |
| 2005/0055058 A1 | 3/2005 | Mower | |
| 2005/0065568 A1 | 3/2005 | Liu et al. | |
| 2005/0102002 A1 | 5/2005 | Salo et al. | |
| 2005/0216066 A1 | 9/2005 | Auricchio et al. | |
| 2006/0069322 A1 | 3/2006 | Zhang et al. | |
| 2006/0247698 A1 * | 11/2006 | Burnes et al. | 607/9 |
| 2008/0255629 A1 | 10/2008 | Jenson et al. | |

OTHER PUBLICATIONS

File History for U.S. Appl. No. 11/601,216.
Office Action Response submitted Mar. 17, 2010 to office action dated Dec. 18, 2009 fro U.S. Appl. No. 11/601,216, 10 pages.
Office Action Response submitted Oct. 13, 2009 to office action dated Jul. 13, 2009 from U.S. Appl. dated Jul. 13, 2009 from U.S. Appl. No. 11/601,216, 9 pages.
Restriction Response submitted May 26, 2009 to restriction requirement dated Apr. 24, 2009 from U.S. Appl. No. 11/601,216, 6 pages.
Restriction Requirement submitted Apr. 24, 2009 from U.S. Appl. No. 11/601,216, 7 pages.
Office Action Response dated Mar. 17, 2009 from European Application No. 07796501.0, 14 pages.
Office Action dated Oct. 30, 2009 from European Application No. 07796501.0, 4 pages.
Office Action Response dated Apr. 28, 2010 from European Application No. 07796501.0, 9 pages.
Office Action Response dated Oct. 23, 2009 from European Application No. 07867460.3, 7 pages.
Office Action dated Jun. 7, 2010 from European Application No. 07867460.3, 5 pages.
File History for EP Application No. 07796501.0 as retrieved from the European Patent Office Electronic File System on Nov. 1, 2011, 231 pages.
File History for EP Application No. 07867460.3 as retrieved from the European Patent Office Electronic File System on Nov. 1, 2011, 79 pages.
File History for EP Application No. 07796501.0 as retrieved from the European Patent Office Electronic File System on Feb. 17, 2012, 235 pages.
Office Action dated Feb. 14, 2012 from JP Application No. 2009-537206, 5 pages.
File History for EP Application No. 07796501.0 as retrieved from the European Patent Office Electronic File System on May 31, 2012, 285 pages.
File History for EP Application No. 07867460.3 as retrieved from the European Patent Office Electronic File System on Jul. 25, 2012, 176 pages.

* cited by examiner

SELECTION OF PACING SITES TO ENHANCE CARDIAC PERFORMANCE

RELATED APPLICATIONS

This application is a continuation of U.S. patent application Ser. No. 11/479,877 filed on Jun. 30, 2006, now U.S. Pat. No. 8,620,430, which is incorporated herein by reference.

FIELD OF THE INVENTION

The present invention relates generally to cardiac pacing therapy, and more specifically, to selection of electrodes and related pacing configuration parameters used to pace a heart chamber.

BACKGROUND OF THE INVENTION

When functioning normally, the heart produces rhythmic contractions and is capable of pumping blood throughout the body. The heart has specialized conduction pathways in both the atria and the ventricles that enable the rapid conduction of excitation impulses (i.e. depolarizations) from the SA node throughout the myocardium. These specialized conduction pathways conduct the depolarizations from the SA node to the atrial myocardium, to the atrio-ventricular node, and to the ventricular myocardium to produce a coordinated contraction of both atria and both ventricles.

The conduction pathways synchronize the contractions of the muscle fibers of each chamber as well as the contraction of each atrium or ventricle with the opposite atrium or ventricle. Without the synchronization afforded by the normally functioning specialized conduction pathways, the heart's pumping efficiency is greatly diminished. Patients who exhibit pathology of these conduction pathways can suffer compromised cardiac output.

Cardiac rhythm management devices have been developed that provide pacing stimulation to one or more heart chambers in an attempt to improve the rhythm and coordination of atrial and/or ventricular contractions. Cardiac rhythm management devices typically include circuitry to sense signals from the heart and a pulse generator for providing electrical stimulation to the heart. Leads extending into the patient's heart chamber and/or into veins of the heart are coupled to electrodes that sense the heart's electrical signals and for delivering stimulation to the heart in accordance with various therapies for treating cardiac arrhythmias.

Pacemakers are cardiac rhythm management devices that deliver a series of low energy pace pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing one or more heart chambers.

Pacing therapy has been used in the treatment of congestive heart failure (CHF). CHF causes diminished pumping power of the heart, resulting in the inability to deliver enough blood to meet the demands of peripheral tissues. CHF may cause weakness, loss of breath, and build up of fluids in the lungs and other body tissues. CHF may affect the left heart, right heart or both sides of the heart. For example, CHF may occur when deterioration of the muscles of the heart produce an enlargement of the heart and/or reduced contractility. The reduced contractility decreases the cardiac output of blood and may result in an increased heart rate. In some cases, CHF is caused by unsynchronized contractions of the left and right heart chambers, denoted atrial or ventricular dysynchrony. Particularly when the left or right ventricles are affected, the unsynchronized contractions can significantly decrease the pumping efficiency of the heart.

Pacing therapy to promote synchronization of heart chamber contractions to improve cardiac function is generally referred to as cardiac resynchronization therapy (CRT). Some cardiac pacemakers are capable of delivering CRT by pacing multiple heart chambers. Pacing pulses are delivered to the heart chambers in a sequence that causes the heart chambers to contract in synchrony, increasing the pumping power of the heart and delivering more blood to the peripheral tissues of the body. In the case of dysynchrony of right and left ventricular contractions, a biventricular pacing therapy may pace one or both ventricles. Bi-atrial pacing or pacing of all four heart chambers may alternatively be used.

SUMMARY OF THE INVENTION

The present invention is directed to systems and methods for selection of electrodes and related pacing configuration parameters used to pace a heart chamber. One embodiment involves a method, implementable by a cardiac therapy system, for delivering pacing therapy to a heart. A change in the hemodynamic state of a patient is detected. Responsive to the detected change, a distribution of an electrical, mechanical, or electromechanical parameter related to contractile function of a heart chamber with respect to locations of multiple electrodes disposed within the heart chamber is determined. A pacing output configuration, including one or more electrodes of the multiple electrodes, is selected and the heart chamber is paced using the selected pacing output configuration.

The change in the hemodynamic state may include, for example, a chronic change or an acute change. In various implementations, the hemodynamic state chamber detected may include a change in at least one of heart rate, activity, posture, respiration rate, minute ventilation, cardiac output, blood chemistry, cardiac dysynchrony, pressure, blood oxygen concentration, impedance, heart rate variability, heart sounds, AV interval, and QRS width. For example, detecting the change in hemodynamic state may involve detecting increased or decreased metabolic demand.

Determination of the parameter distribution may involve determining one or more electrical cardiac parameters such as depolarization characteristics including depolarization delays, atrioventricular timing intervals, depolarization amplitude, depolarization-repolarization intervals, depolarization thresholds, and/or other depolarization characteristics. Determination of the parameter distribution may involve determining one or more mechanical cardiac parameters such as hypertrophy, wall stress, wall strain, peak displacement, peak velocity, peak strain, minimum displacement, minimum velocity, minimum strain, time to peak or minimum displacements, velocities, and strain, among other mechanical parameters. Determination of the parameter distribution may involve determining one or more electromechanical cardiac parameters such as interval from electrical depolarization time to peak strain, or other combinations of the electrical and mechanical properties.

The selection of the electrode configuration may involve selecting one or more electrodes disposed at locations having longer depolarization delays relative to depolarization delays of other locations. In one implementation, one or more previously selected electrodes and one or more additional electrodes may be selected, where the one or more previously selected electrodes are associated with the longest depolarization delays and the one or more additional electrodes associated with the next longest depolarization delays. The heart chamber may be paced by delivering pacing pulses to the selected electrodes in a timed sequence based on the parameter distribution.

In certain embodiments, information related to the change in hemodynamic status, parameter distribution, and pacing output configuration is stored. A lookup table may be generated based on the stored information. A subsequent pacing output configuration may be selected based information stored in the lookup table. The stored information may be displayed to a health care professional or used for analysis at a later time, for example.

Another embodiment of the invention is directed to a cardiac therapy system. The therapy system includes multiple electrodes respectively positionable at multiple locations within a heart chamber. One or more sensors and associated detection circuitry are configured to detect a change in a patient's hemodynamic state. A processor is configured to determine a distribution of a parameter related to the contractile function of the heart chamber with respect to the multiple electrode locations responsive to a detected change in the hemodynamic state. Selection circuitry is used to select one or more of the multiple electrodes based on the measured parameter. A pulse generator delivers pacing therapy to the heart chamber via the selected electrodes.

The paced chamber may include a ventricle or an atrium, or multiple chambers may be paced by the cardiac therapy system via selectable pacing output configurations for each paced chamber.

The one or more sensors and associated circuitry configured to detect the change in hemodynamic state may include, for example, sensors and circuitry configured to sense and detect physiological parameters related to hemodynamic state including transthoracic impedance, respiration rate, minute ventilation, heart rate, cardiac dysynchrony, activity, posture, blood chemistry, O2 saturation, heart sounds, wall stress, wall strain, hypertrophy, inter-electrode impedance, electrical delays (PR interval, AV interval, QRS width, etc.), activity, cardiac chamber pressure, cardiac output, temperature, heart rate variability, depolarization amplitudes, depolarization timing, and/or other physiological parameters.

In some implementations, the selection circuitry is configured to determine a timing sequence for pacing pulses delivered to the one or more electrodes based on the parameter distribution. In these implementations, the pulse generator is configured to deliver the pacing pulses to the one or more electrodes according to the timing sequence. In some implementations, the selection circuitry is configured to select amplitudes for pacing pulses delivered to the one or more electrodes based on the parameter distribution. In these implementations, the pulse generator is configured to deliver the pacing pulses to the one or more electrodes at the selected amplitudes.

In certain embodiments, at least one of the detection circuitry, the processor, and the selection circuitry comprises a patient-external component. In other embodiments, the detection circuitry, processor, and selection circuitry are fully implantable.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
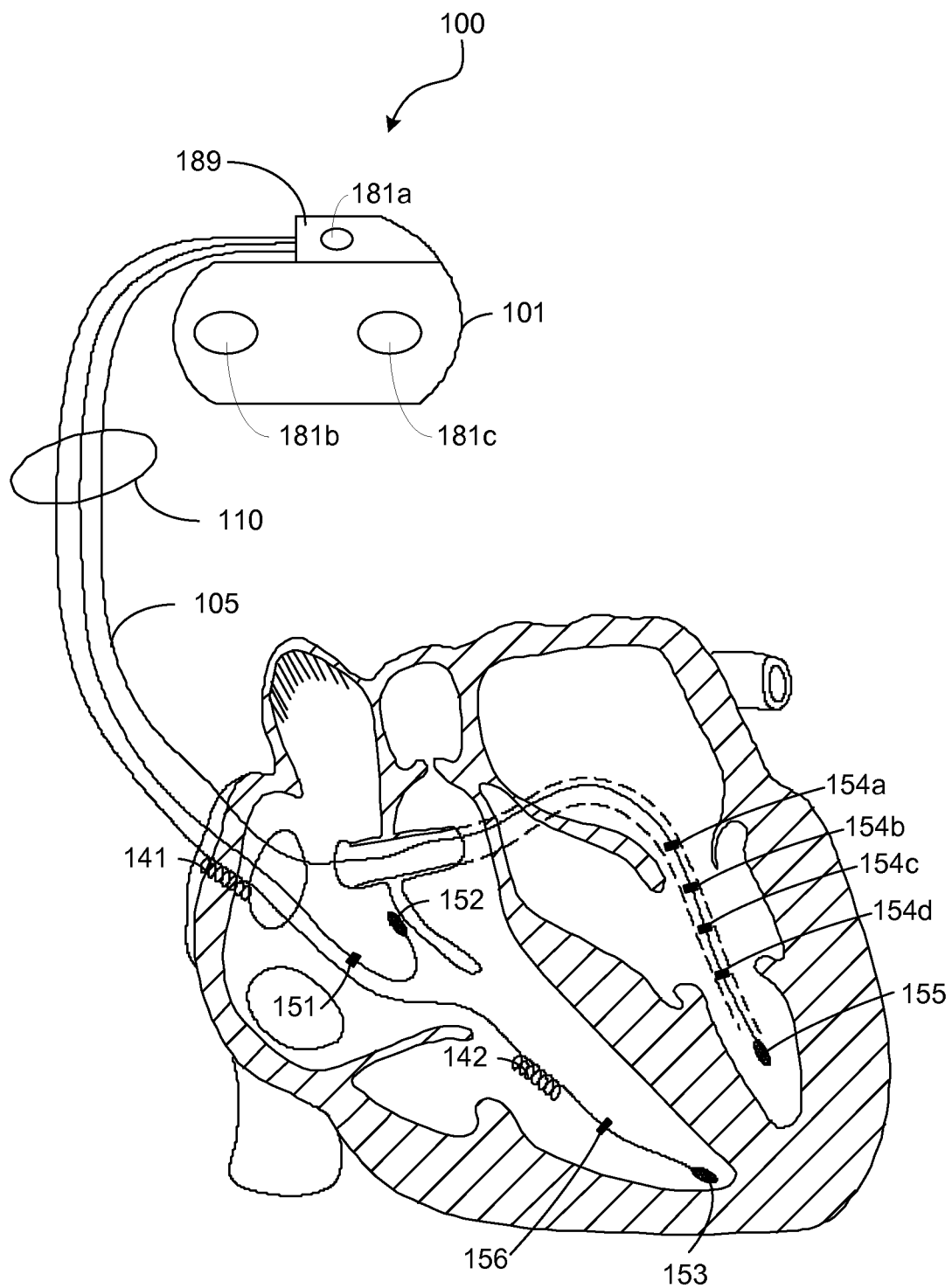
FIG. 1 illustrates a patient-implantable device that may be used in conjunction with selection of pacing output configuration for delivery of stimulation pulses in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

Systems, devices or methods according to the present invention may include one or more of the features, structures, methods, or combinations thereof described hereinbelow. For example, a device or system may be implemented to include one or more of the advantageous features and/or processes described below. It is intended that such device or system need not include all of the features described herein, but may be implemented to include selected features that provide for useful structures and/or functionality. Such a device or system may be implemented to provide a variety of therapeutic or diagnostic functions.

A cardiac therapy device may deliver electrical stimulation pulses to one or more electrodes disposed within the heart chamber and/or otherwise electrically coupled to the myocardium to initiate contractions of the chamber. Embodiments of the invention are directed to systems and methods for selection of one or more electrodes disposed within a heart chamber for application of pacing pulses. The pacing pulses may be delivered via the selected electrodes in accordance with timing and/or amplitude/pulse waveform output configurations that provide improved contractile function of the chamber.

The therapy device 100 illustrated in FIG. 1 is an embodiment of a patient-implantable device that may be used in conjunction with selection of electrodes, timing sequences, and/or amplitude/pulse width (collectively referred to herein as pacing output configuration) for delivery of stimulation pulses. The therapy device 100 includes cardiac rhythm management (CRM) circuitry enclosed within an implantable housing 101. The CRM circuitry is electrically coupled to an intracardiac lead system 110.

Portions of the intracardiac lead system 110 are inserted into the patient's heart. The lead system 110 includes cardiac pace/sense electrodes 151-156 positioned in, on, or about one or more heart chambers for sensing electrical signals from the patient's heart and/or delivering pacing pulses to the heart. The intracardiac sense/pace electrodes 151-156, such as those illustrated in FIG. 1, may be used to sense and/or pace one or more chambers of the heart, including the left ventricle, the right ventricle, the left atrium and/or the right atrium. The lead system 110 includes one or more defibrillation electrodes 141, 142 for delivering defibrillation/cardioversion shocks to the heart.

The left ventricular lead 105 incorporates multiple electrodes 154a-154d positioned at various locations within, on or about the left ventricle. Stimulating the ventricle at multiple locations or at a single selected location may provide for increased cardiac output in a patients suffering from CHF. In accordance with various embodiments described herein, one or more of the electrodes 154a-154d are selected for pacing the left ventricle. In other embodiments, leads having multiple pacing electrodes positioned at multiple locations within a chamber, such as the one illustrated by the left ventricular lead 105 of FIG. 1, may be implanted within any or all of the heart chambers. A set of electrodes positioned within one or more chambers may be selected. Electrical stimulation pulses may be delivered to the chambers via the selected electrodes according to a timing sequence and output configuration that enhances cardiac function.

Portions of the housing 101 of the implantable device 100 may optionally serve as one or multiple can or indifferent electrodes. The housing 101 is illustrated as incorporating a header 189 that may be configured to facilitate removable attachment between one or more leads and the housing 101. The housing 101 of the therapy device 100 may include one or more can electrodes 181b, 181c. The header 189 of the therapy device 100 may include one or more indifferent electrodes 181a. The housing 101 and/or header 189 may include any number of electrodes positioned anywhere in or on the housing 101 and/or header 189.

The cardiac electrodes and/or other sensors disposed within or on the housing 101 or lead system 110 of the therapy device 100 may produce signals used for detection and/or measurement of various physiological parameters, such as transthoracic impedance, respiration rate, minute ventilation, heart rate, cardiac dysynchrony, activity, posture, blood chemistry, O2 saturation, heart sounds, wall stress, wall strain, hypertrophy, inter-electrode impedance, electrical delays (PR interval, AV interval, QRS width, etc.), activity, cardiac chamber pressure, cardiac output, temperature, heart rate variability, depolarization amplitudes, depolarization timing, and/or other physiological parameters.

For example, in some configurations, the implantable device 100 may incorporate one or more transthoracic impedance sensors that may be used to acquire the patient's respiratory waveform, and/or to acquire other respiratory-related information. The transthoracic impedance sensor may include, for example, one or more intracardiac electrodes 141, 142, 151-156 positioned in one or more chambers of the heart. The intracardiac electrodes 141, 142, 151-156 may be coupled to impedance drive/sense circuitry positioned within the housing 101 of the therapy device 100. Information from the transthoracic impedance sensor may be used to adapt the rate of pacing to correspond to the patient's activity or metabolic need.

Communications circuitry is disposed within the housing 101 for facilitating communication between the CRM circuitry and a patient-external device, such as an external programmer or advanced patient management (APM) system. The communications circuitry may also facilitate unidirectional or bidirectional communication with one or more implanted, external, cutaneous, or subcutaneous physiologic or non-physiologic sensors, patient-input devices and/or information systems.

In certain embodiments, the therapy device 100 may include circuitry for detecting and treating cardiac tachyarrhythmia via defibrillation therapy and/or anti-tachyarrhythmia pacing (ATP). Configurations providing defibrillation capability may make use of defibrillation coils 141, 142 for delivering high energy shocks to the heart to terminate or mitigate tachyarrhythmia.

In some embodiments, the implantable therapy device 100 may include circuitry for selection of pacing electrode(s), timing sequence, and/or amplitude or pulse waveform output configurations (referred to collectively herein as the pacing output configuration) to be applied via one or multiple electrodes within one or multiple heart chambers. In other embodiments, the therapy device 100 may transfer sensed or derived information relevant to pacing output configuration to a patient-external device. Following download of the implantably sensed or derived information, selection of the pacing output configuration may be made by the patient-external device or may be made by a clinician using information provided via the patient-external device.

Pacing output configuration involves selection of the site or sites of pacing within a heart chamber and/or the temporal sequence of the pacing pulses delivered to the multiple sites, and may also optionally involve selection of particular pulse characteristics (e.g., amplitude, duration, anodal/cathodal polarity, and waveshape) used for the pacing pulses. Selection of the pacing output configuration is particularly desirable for optimal application of cardiac resynchronization therapy. Congestive heart failure, long term pacing, ischemia, myocardial infarction and/or other factors can produce non-uniformities in the electrical, mechanical or electromechanical properties of the myocardium. These non-uniformities can cause a heart chamber to contract in an uncoordinated manner resulting in inefficient pumping action. The location of the pacing site or sites and/or other properties of the pacing output configuration affects the spread of the depolarization excitation which in part determines the manner in which the chamber contracts. In a pacemaker equipped with multiple pacing electrodes respectively disposed at multiple pacing sites within a heart chamber, the ability to select one or more electrodes, temporal sequence, and/or pulse waveform characteristics for delivery of pacing can be used enhance the contractile function of the heart chamber.

Multi-site pacemakers, such as illustrated herein, are capable of delivering pacing pulses to multiple sites of the atria and/or ventricles during a cardiac cycle. Certain patients may benefit from activation of parts of a heart chamber, such as a ventricle, at different times in order to distribute the pumping load and/or depolarization sequence to different areas of the ventricle. A multi-site pacemaker has the capability of switching the output of pacing pulses between selected electrodes or groups of electrodes within a heart chamber during different cardiac cycles. For example, the pacing pulses may be delivered to the heart chamber at specified locations and at specified times during the cardiac cycle to enhance the synchrony of the contraction. Amplitude, pulse duration, anodal/cathodal polarity and/or waveshape of the pacing pulses may also be altered to enhance pumping function.

Figure 2:
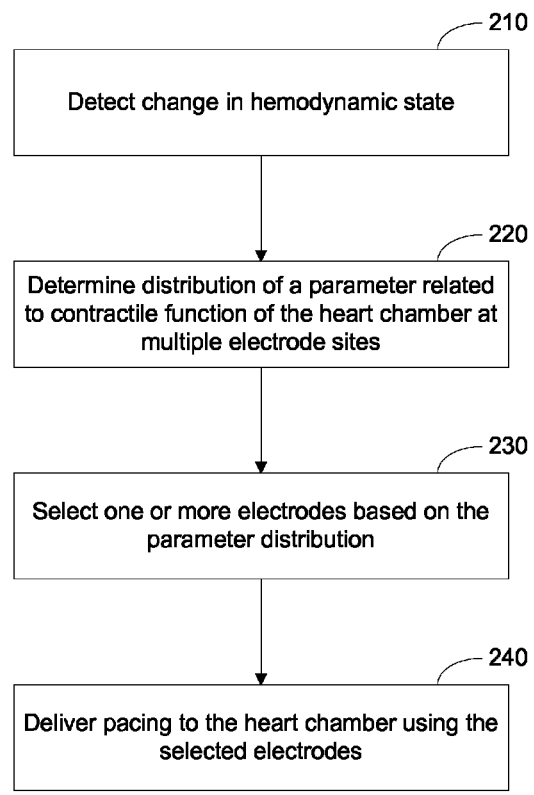
FIG. 2 is a flow graph illustrating a process for pulse output configuration in accordance with embodiments of the invention.

FIG. 2 is a flow graph illustrating an approach for pulse output configuration in accordance with one approach. In this example, optimization of the pulse output configuration is triggered based on a change the patient's hemodynamic status. According to one approach, a sensor or other device is used to detect 210 a change that indicates the patient's hemodynamic status has changed. The change in hemodynamic status may be indicated based on acute or chronic changes. For example, an acute or chronic change in hemodynamic status may be indicated by changes in heart rate, respiration rate, minute ventilation, tidal volume, posture, O2 saturation, cardiac dysynchrony, medication, progression of CHF, fluid retention, dyspnea, disordered breathing, weight gain, decreased level of activity, posture, posture correlated to periods of sleep, duration of pacing therapy, disease status, ischemia, myocardial infarction, and/or other changes indicative of a change in hemodynamic status of the patient.

A detected change in the patient's hemodynamic status may indicate a need to adjust the pulse output configuration to achieve optimal pacing therapy for the patient's changed status. Responsive to the detected change in hemodynamic status, the contractile function of at least one heart chamber is assessed 220 by determining the distribution of an electrical, mechanical or electromechanical parameter related to contractile function of the chamber with respect to locations of multiple electrodes disposed within the heart chamber. The pacing output configuration, including selection 230 of one or more electrodes, is determined based on the distribution of the parameter. The heart chamber is paced 240 using the selected electrodes.

In one example, change in hemodynamic status involves an increase or decrease in metabolic demand as indicated by a change in heart rate. In this example, the parameter related to contractile function comprises the timing of the spread of a depolarization wavefront within a heart chamber. Depolarization delays from site to site within a heart chamber may change as a function of heart rate. Thus, an electrode or electrodes previously selected for pacing at a baseline heart rate may no longer produce an optimal contraction of the heart chamber at an elevated heart rate due to changes in the depolarization delays across the heart chamber when the heart rate is elevated. The distribution of depolarization delays at the multiple electrode sites is determined. The pulse output configuration is re-optimized for the elevated rate by altering the electrode or electrodes selected for pacing, such as by selecting one or more electrodes associated with the longest depolarization delays as the pacing electrodes.

Optimization of the pacing output configuration may be used to prevent or reverse the effects of undesirable remodeling due to ischemia or myocardial infarction (MI). Changes in cardiac ischemia or MI conditions are associated with changes in the distribution of wall stress within a heart chamber. In one example, detection of changes in cardiac ischemia or MI conditions indicates a change in hemodynamic status. Responsive to this change, electrodes for pacing may be selected so that a minimal amount of stress is placed on an affected region. In other configurations, the electrodes may be selected to produce a uniform stress distribution, or to pre-excite a stressed region of the myocardium relative to other regions.

Figure 3:
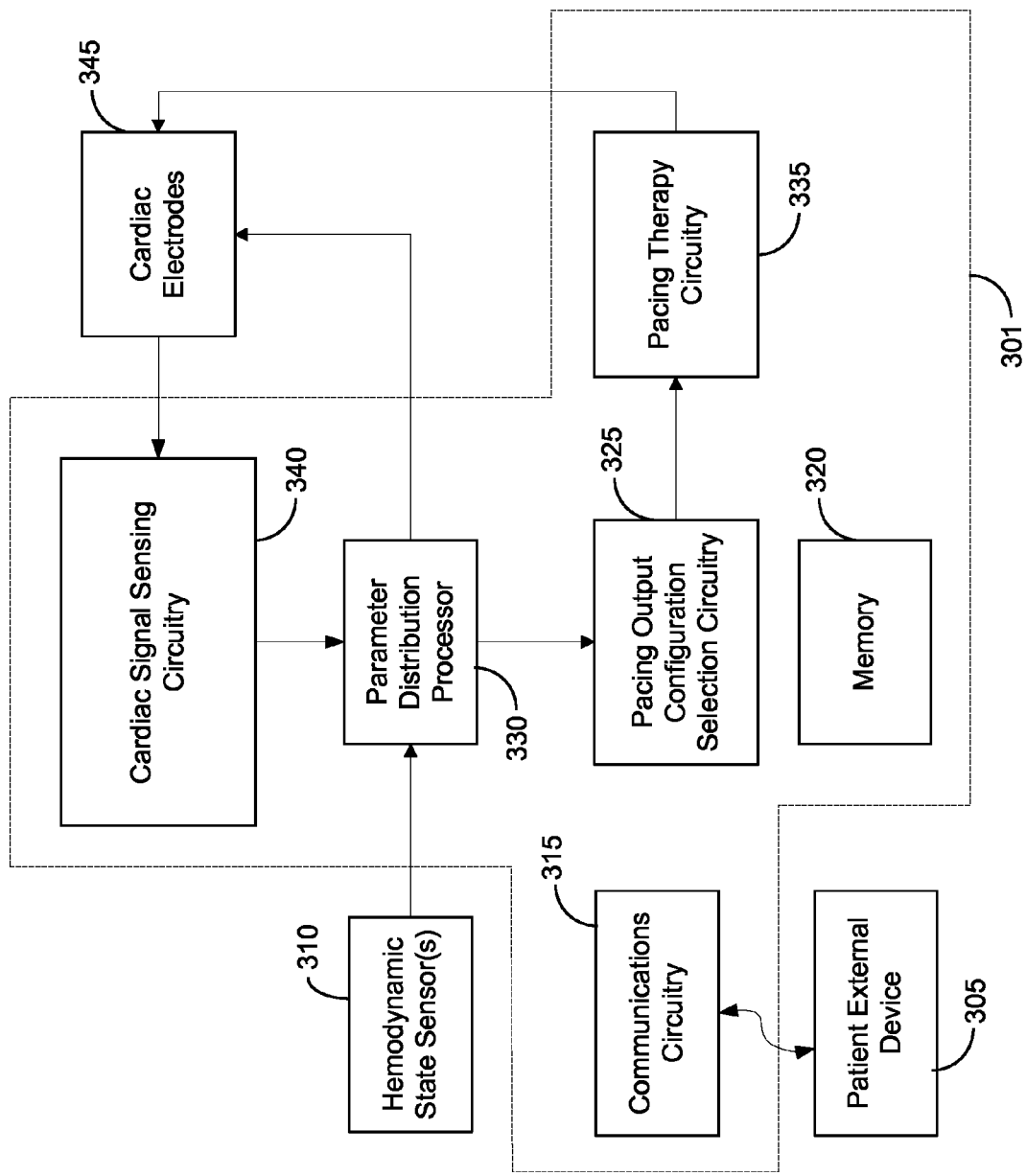
FIG. 3 is a block diagram of circuitry used for selection of the pulse output configuration in accordance with embodiments of the invention.

FIG. 3 is a block diagram of circuitry used for selection of the pulse output configuration in accordance with embodiments of the invention. Multiple cardiac electrodes 345 are disposed at multiple locations within a heart chamber. One or more sensors 310 are configured to sense physiological factors indicative of a patient's hemodynamic status. Responsive to a detected change in hemodynamic status, determination of the distribution of one or more parameters related to the contractile function of the heart is triggered. The parameter distribution may indicate that a change in the pacing output configuration would be beneficial. In various implementations, the hemodynamic status indicators used to trigger determination of the pacing output configuration may be selectable by the therapy device or programmable by a clinician.

The parameter distribution processor 330 assesses the distribution of an electrical, mechanical or electromechanical parameter related to contractile function of the heart chamber. For example, the parameter distribution processor 330, in conjunction with the cardiac electrodes 345, may assess the distribution of an electrical cardiac parameter at each of the electrode locations. For example, electrical cardiac parameters may include depolarization characteristics such as depolarization delays, atrioventricular timing intervals, depolarization amplitude, depolarization-repolarization intervals, depolarization thresholds, and/or other depolarization characteristics. The parameter distribution processor 330, may assess the distribution of mechanical cardiac parameters such as hypertrophy, wall stress, wall strain, peak displacement, peak velocity, peak strain, minimum displacement, minimum velocity, minimum strain, time to peak or minimum displacements, velocities, and strain, among other mechanical parameters. The parameter distribution processor 330 may assess the distribution of electromechanical cardiac parameters such as interval from electrical depolarization time to peak strain, or other combinations of the electrical and mechanical properties.

In one embodiment, depolarization delays may be measured at each electrode site during an intrinsic systolic contraction. The distribution of depolarization delays can be determined by measuring the timing of R-wave peaks detected via cardiac electrograms sensed at each of the cardiac electrodes during the contraction.

In accordance with some embodiments, cardiac sensing circuitry 340 may include individual sense amplifiers and peak detectors for each electrode in the ventricle. In other embodiments, a bipolar sensing technique may be used to reduce the number of sense amplifiers and/or other signal processing circuitry required to detect the depolarization delay distribution. Measurement of the distribution of depolarization delays in a heart chamber may be accomplished using the techniques described in commonly owned U.S. Patent Publications 2004/0098056 or 2004/0102812 which are incorporated herein by reference.

After measurement of the distribution of the parameter related to contractile function, selection circuitry 325 selects an appropriate pacing output configuration. According to one aspect, the selection circuitry 325 may select an electrode corresponding to a pacing site having a longest depolarization delay or may select a number of electrodes for pacing in a pattern or sequence based on their respective conduction delays. In some configurations, the electrode associated with the longest delay may be paced first, the electrode associated with the second longest delay may be paced next, and so forth.

As described above, one way of selecting a pacing site for resynchronization therapy is to measure the depolarization delays of potential pacing sites. One or more sites that are demonstrated to be excited later in the contraction sequence may then be selected as pacing sites. Pacing the latest activated site, or pacing multiple sites in a sequence corresponding to their respective conduction delays may provide a more coordinated contraction.

Changes in the presence of areas of ischemia, scar tissue or infarction may cause changes in wall stress within a cardiac chamber. Resynchronization pacing may be applied to the stressed myocardial regions so that the stress at the high stress regions is decreased, such as by reducing the preload and afterload to which the region is subjected.

In various embodiments, re-optimization of the pacing output configuration may be triggered by detection of an increased heart rate, ischemia, or MI, for example. The parameter distribution processor 330 assesses the distribution of wall stress in the heart chamber. For example, distribution of wall stress may be accomplished by measuring the action potential duration at each electrode during systole. Measurement of the action potential durations may be implemented by sensing an electrogram at each electrode during a cardiac cycle and measuring the time between a depolarization and a repolarization at each electrode.

In one embodiment, determination of wall stress distribution and reoptimization of the pacing output configuration may be based on the phenomena of mechanical alternans. When oscillations in pulse pressure are detected in a patient, referred to as pulse alternans, it is generally interpreted as a sign of left ventricular dysfunction. Localized alternations in local wall stress, as revealed by alternations in the action potential duration may similarly indicate that the site is subject to increased stress. The stress distribution at the electrode sites may be identified by detecting the degree of oscillation in the measured action potential duration at the electrode sites.

Sites that are most stressed may be identified as those sites having smallest action potential duration and/or the greatest amount of oscillation in the action potential duration. The selection circuitry 325 may determine the pacing output configuration by selecting a site exhibiting a high stress relative to the stress at other sites as the pacing electrode site. In another approach, the selection circuitry 325 selects a number of sites of pacing, wherein the sites are paced in a sequence based on the relative amount of wall stress detected at each of the sites. Sites exhibiting relatively higher levels of wall stress may be pre-excited with respect to sites exhibiting relatively lower levels of wall stress. Techniques for assessing wall stress are described in commonly owned U.S. Pat. No. 6,965,797 which is incorporated herein by reference.

In some embodiments, detection of a change in hemodynamic status may trigger an assessment of the distribution of hypertrophy exhibited by a cardiac chamber. Hypertrophy refers to a thickening of the myocardial tissue. Congestive heart failure may cause an increase of the diastolic filling pressure of the ventricles which increases the ventricular preload (i.e., the degree to which the ventricles are stretched by the volume of blood in the ventricles at the end of diastole). CHF can be at least partially compensated by this mechanism. However, when the ventricles are stretched due to increased preload over a period of time, the ventricles become dilated. The enlargement of the ventricular volume causes increased ventricular wall stress at a given systolic pressure. This phenomenon stimulates hypertrophy of the ventricular myocardium. Sustained stresses causing hypertrophy may cause death of the cardiac muscle cells, wall thinning and further deterioration in cardiac function. Thus, it is desirable to identify hypertrophic areas and apply pacing in such a way that the stressed areas area unloaded.

A depolarization wavefront propagating through a hypertrophied myocardial region results in a greater potential being measured by a sensing electrode due to the increased muscle mass of the hypertrophied region. During depolarization, the electrogram signal measured at an electrode disposed near a relatively hypertrophied region has a greater amplitude than a signal measured from an electrode near an unhypertrophied region. In one embodiment, the distribution of hypertrophic myocardial tissue in the heart chamber is determined. Hypertrophy at each electrode site may be determined by the parameter distribution processor 330 based on the amplitude of electrogram signal measured at each electrode.

The pacing output configuration may be determined based on the relative amplitudes of electrogram signals detected at each of the electrode sites. The pacing output configuration is selected by the selection circuitry 325 so that hypertrophic regions are mechanically unloaded during pacing.

In some embodiments, changes in hypertrophy may be determined by measuring electrical impedance between the electrodes or through sonomicrometry measurements. For example, changes in hypertrophy of a cardiac chamber may be measured via an array of implanted piezoelectric sonomicrometer transducers disposed within the chamber.

After selection of the pacing output configuration by any of the methods described above, pacing is delivered by the pacing therapy circuitry 335 via the selected electrode(s).

In some embodiments, the parameter distribution processor 330 and pacing output selection circuitry 325 may include functionality to initiate determination of the pacing output configuration based on a plurality of hemodynamic status indicators. Signals associated with the patient's hemodynamic status may be generated by multiple sensors. If the value of one or more of the signals changes beyond a threshold level, then a determination of the pacing output configuration may be triggered. In some implementations, determination of the pacing output configuration is based on a relationship between the values of two or more sensor signals. For example, an increase in disordered breathing with a concurrent decrease in activity may indicate a worsening of CHF. The pacing output configuration may be re-optimized if an increase in disordered breathing above a predetermined threshold is detected concurrently with a decrease in activity below a predetermined threshold.

In some configurations, the parameter distribution processor 330 is capable of determining more than one electromechanical parameter distribution. One or more distributions used to configure the pacing output configuration may be selected by the device or programmed by a clinician. In one configuration, the one or more electromechanical parameter distributions used to configure the pacing output may be related to the hemodynamic status indicators. For example, if a particular hemodynamic status indicator that is more closely related to the likelihood of wall stress triggers the pacing output configuration process, then wall stress may be selected as the electromechanical parameter distribution used for pacing output configuration.

In another configuration, the one or more electromechanical parameter distributions used to configure the pacing output may be selected based on the goals of the pacing output configuration. The goals of the pacing output configuration may be determined by the device or programmed by a clinician. For example, if a goal of the pacing output configuration is to reduce ventricular dysynchrony, then the pacing output configuration may be based on the distribution of depolarization delay. If a goal of the pacing output configuration is to reduce remodeling due to wall stress, then the pacing output configuration may be based on the distribution of wall stress. Using the wall stress distribution to select the pacing output configuration to reduce remodeling may be more effective than using depolarization delay distribution because myocardial regions that are subjected to the highest levels of mechanical stress during contractions may not always correspond to the sites with the largest conduction delay due to the presence of scar tissue or areas of infarction.

Circuitry for determining the distribution of an electromechanical parameter related to contractile function and to select a pacing output configuration may be provided in a therapy device. In one embodiment, the processes included within the dashed line 301 of FIG. 3 may be provided by an implantable therapy device such as the implantable device illustrated in FIG. 1. Such a device may include a power supply (not shown) and memory 320 for storing program instructions and/or data. In various configurations, the memory may be used to store information including information about the change in hemodynamic condition, the parameter distribution assessment, and/or the pacing output configuration. The information stored in the memory may be used to create a lookup table for future reference that may be used to select the pacing output configuration if a subsequent similar change in the hemodynamic condition is observed. In addition, the stored information may be used to provide a log of events for display or analysis at a later time. The device also includes communications circuitry 315 for communicating with a patient-external device 305 such as a programmer or advanced patient management system.

In some configurations, the implantable device may provide some of the functionality for selection of pacing output configuration, and a patient-external device may provide some of the functionality. For example, in one embodiment, the patient-external device communicates with the implantable device over a telemetry link and receives either raw data, markers corresponding to particular sensed events, and/or measurements of timing intervals or other signal characteristics as determined by the implantable device. The external device may then determine the electromechanical parameter distribution and compute optimal settings for the pacing output configuration which are either transmitted to the implantable device for immediate reprogramming, or presented to a clinician operating the external device as a recommendation. Alternatively, the external device may present the raw data, markers and/or measurements to the clinician who then programs the implantable device in accordance with an algorithm.

In some implementations, an advanced patient management (APM) system remotely monitors the patient's hemodynamic status. If a change in hemodynamic status is detected, the APM system signals the implantable device to initiate determination of the electromechanical parameter distribution. In some scenarios selection of the pacing output configuration may be performed by the implantable device. In other scenarios, the APM system may perform the selection. Various therapeutic and/or diagnostic medical devices coupled to the APM system can provide sensing capability for use in detecting the patient's hemodynamic state via a multi-sensor approach. The APM system may be coupled to a variety of patient-external and patient-implantable devices, each device incorporating a set of sensors which are remotely accessible to the APM system.

A user interface may be coupled to the APM allowing a physician to remotely monitor cardiac functions, as well as other patient conditions. The user interface may be used by the clinician to access information available via the APM. The clinician may also enter information via the user interface for setting up the pacing output configuration functionality. For example, the clinician may select particular sensors, hemodynamic status indicators, indicator levels or sensitivities, and/or electromechanical parameters. Methods, structures, and/or techniques described herein, may incorporate various APM related methodologies, including features described in one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

Figure 4:
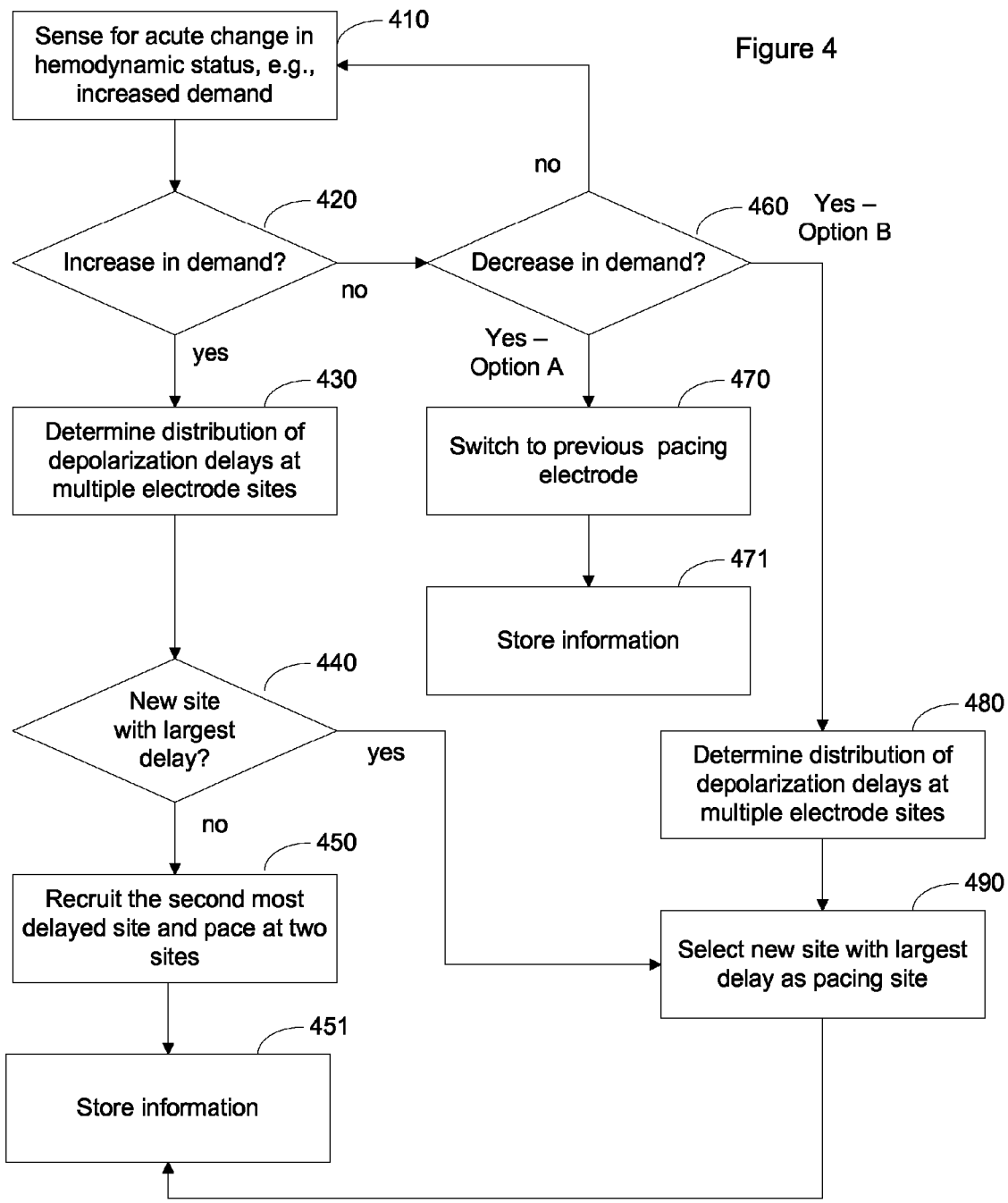
FIG. 4 is a flow diagram illustrating a process of for determining pacing output configuration triggered by an indication of an acute change in hemodynamic status in accordance with embodiments of the invention.

FIG. 4 is a flow diagram illustrating a process of for determining pacing output configuration in accordance with an embodiment of the invention. In this embodiment, the system senses for 410 indicators of an acute change in hemodynamic status. For example, an acute change in homodynamic status may include be detected based on changes in posture, O2 level, activity, heart rate, respiration rate, minute ventilation, and/or other factors. In one particular example, an increase in hemodynamic status comprises a change in metabolic demand. If an increase in demand is detected 420, such a change in the hemodynamic demand indicator beyond a baseline level, the system determines 430 the distribution of a depolarization delays at multiple electrode sites. If one or more electrode sites other than those used in the previous (baseline) pulse output configuration have 440 the longest depolarization delays, the system switches 490 the pacing output configuration to include the one or more sites having the longest delay.

If the previous pulse output configuration includes 440 the one or more electrode sites having the longest depolarization delays, the system switches 450 the pacing output configuration to recruit an additional one or more electrodes, such as those one or more electrodes having the second longest depolarization delays.

If the system detects 460 a decrease in hemodynamic demand, such as back to the baseline level, then one of two optional processes may be implemented. According to a first optional process (Option A) the system switches 470 the pacing output configuration to the previously used baseline configuration. According to a second optional process (Option B) the system determines 480 the distribution of the depolarization delays at the multiple sites for the decreased demand condition. The pulse output configuration is selected 490 to include one or more electrode sites having the largest depolarization delays. The change in hemodynamic condition that prompted the pacing configuration change, the measurement of the parameter distribution, and/or the final electrode configuration used for pacing may be stored 451, 471 either in the implantable device or patient-external device. The information stored may be used as a lookup table for subsequent selection of a pacing configuration. Additionally, or alternatively, the stored information may be used to provide a log of events that may be reviewed and/or analyzed at a later time.

Figure 5:
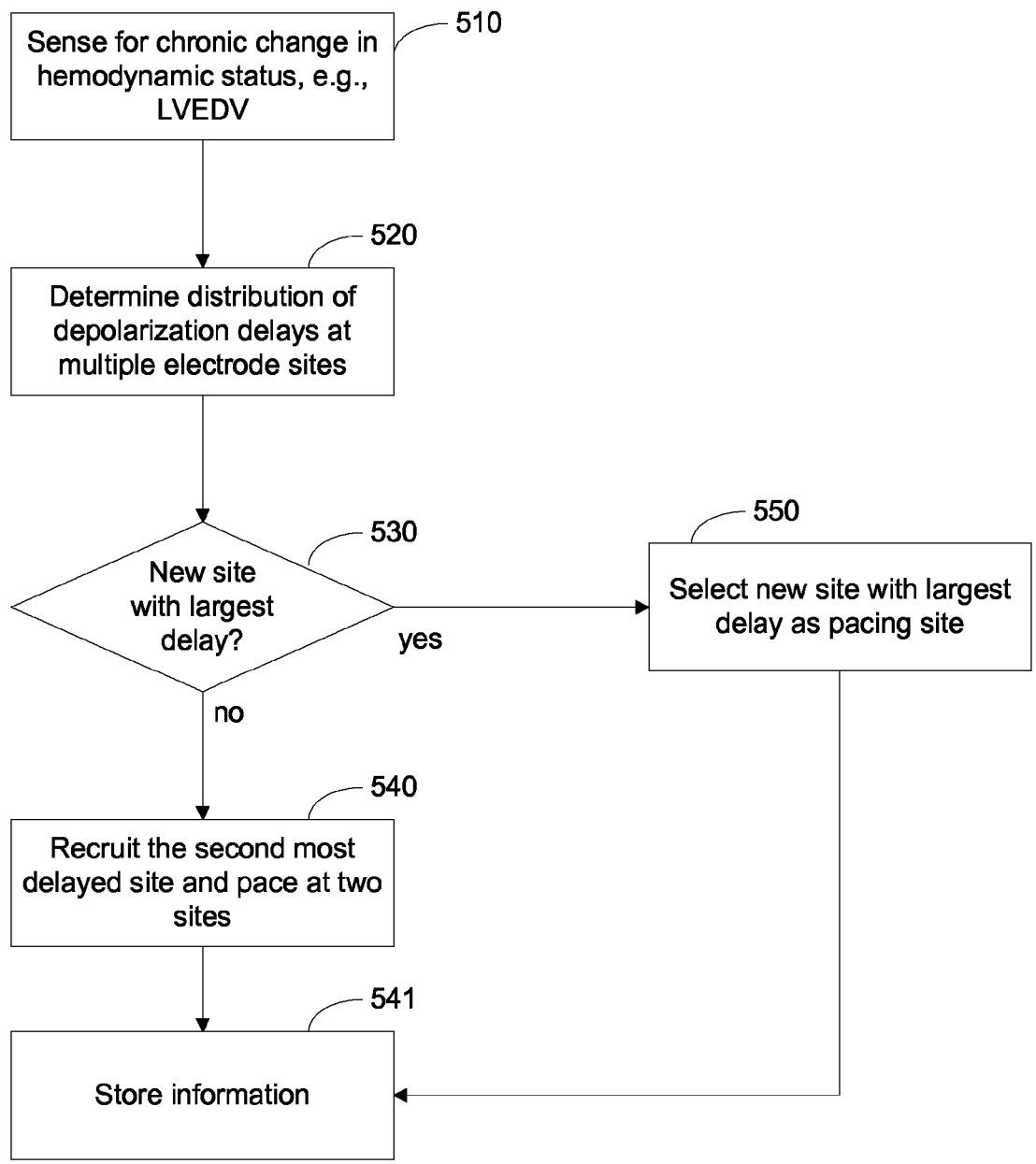
FIG. 5 is a flow graph of a method useful for determining the pacing output configuration when a chronic change in hemodynamic status is indicated in accordance with embodiments of the invention.

FIG. 5 is a flow graph of a method useful for determining the pacing output configuration when a chronic change in hemodynamic status is detected. Chronic changes in hemodynamic status may be indicated by a progression of CHF symptoms, such as increased breathing disorders, elevated posture during sleeping, changes in left ventricular pressures, detection of myocardial infarction, and/or other long-term changes in hemodynamic status. If chronic changes are detected 510, the system re-optimizes the pacing output configuration to provide enhanced pumping function. The system determines 520 the distribution of depolarization delays (or other electromechanical parameters) at multiple electrode sites. If one or more new sites have 530 larger delays than the previously used sites, then the new sites are selected 550 for use in the pulse output configuration. The previously used sites may or may not be excluded from the pulse output configuration. If the previously used sites still have 530 the largest delays, the previously used sites are selected 540 along with one or more additional sites which have the second largest delays. The condition that prompted the pacing configuration change, the measurement of the parameter distribution, and/or the final electrode configuration used for pacing may be stored 541.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A cardiac therapy system, comprising:
multiple electrodes respectively positionable at multiple locations in, on, or about a left ventricle of a heart;
one or more sensors configured to detect a chronic and acute change in a patient's hemodynamic state;
a controller operatively coupled to the one or more sensors for determining when a chronic change in the patient's hemodynamic state occurs, and when an acute change in the patient's hemodynamic state occurs, the controller is further configured to:
in response to determining a chronic change in the patient's hemodynamic state, select a first pacing output configuration including a first subset of electrodes of the multiple electrodes;
in response to determining an acute change in the patient's hemodynamic state, select a second pacing output configuration including a second subset of electrodes of the multiple electrodes, wherein the second subset of electrodes is different from the first subset of electrodes; and
a pulse generator configured to deliver a cardiac resynchronization therapy to the left ventricle using the selected first or second pacing output configuration.

2. The cardiac therapy system of claim 1, wherein the one or more sensors comprises one or more of a chemical sensor, a patient activity sensor, a respiration sensor, and a cardiac electrogram sensor.

3. The cardiac therapy system of claim 1, wherein in response to determining a chronic change in the patient's hemodynamic state, the controller is further configured to:
determine a depolarization delay with respect to each of the multiple electrodes;
determine a distribution of the depolarization delays; and
select the first subset of electrodes of the multiple electrodes based, at least in part, on the determined distribution.

4. The cardiac therapy system of claim 1, wherein in response to determining an acute change in the patient's hemodynamic state, the controller is further configured to:
determine a depolarization delay with respect to each of the multiple electrodes;
determine a distribution of the depolarization delays; and
select the second subset of electrodes of the multiple electrodes based, at least in part, on the determined distribution.

5. A cardiac therapy system, comprising:
multiple electrodes of a multiple electrode lead respectively positionable at multiple locations in, on, or about a left ventricle of a heart;
one or more sensors configured to detect a chronic and an acute change in a patient's hemodynamic state;
a controller operatively coupled to the one or more sensors for determining when a chronic change in the patient's hemodynamic state occurs, and when an acute change in the patient's hemodynamic state occurs, the controller is further configured to:
in response to determining a chronic change in the patient's hemodynamic state, select a first pacing output configuration including a first subset of electrodes of the multiple electrodes;
in response to determining an acute change in the patient's hemodynamic state, select a second pacing output configuration including a second subset of electrodes of the multiple electrodes, wherein the second subset of electrodes is different from the first subset of electrodes;
the controller is further configured to:
determine a depolarization delay with respect to each of the multiple electrodes;
determine a distribution of the depolarization delays;
select the first subset of electrodes of the multiple electrodes based, at least in part, on the determined distribution;
select the second subset of electrodes of the multiple electrodes based, at least in part, on the determined distribution; and
a pulse generator configured to deliver a cardiac resynchronization therapy to the left ventricle using the selected first or second pacing output configuration.

6. The cardiac therapy system of claim 5, wherein:
the controller is further configured to determine a timing sequence for pacing pulses to be delivered to the first subset of electrodes of the first pacing output configuration based, at least in part, on the parameter distribution; and
the pulse generator is configured to deliver the pacing pulses to the first subset of electrodes of the first pacing output configuration according to the timing sequence.

7. The cardiac therapy system of claim 6, wherein:
the controller is further configured to determine a timing sequence for pacing pulses to be delivered to the second subset of electrodes of the second pacing output configuration based, at least in part, on the parameter distribution; and
the pulse generator is configured to deliver the pacing pulses to the second subset of electrodes of the second pacing output configuration according to the timing sequence.

8. The cardiac therapy system of claim 5, wherein the one or more sensors comprises a heart sound sensor.

9. The cardiac therapy system of claim 5 comprising an implantable device, wherein:
the controller is implemented by the implantable device; and
the multiple electrodes, the one or more sensors and the pulse generator are implemented by the implantable device.

10. The cardiac therapy system of claim 5 comprising an external patient management system and an implantable device, wherein:
the controller is at least partially implemented by the external patient management system; and
the multiple electrodes, the one or more sensors and the pulse generator are at least partially implemented by the implantable device.

11. The cardiac therapy system of claim 10, wherein the external patient management system accepts a selection from a user, wherein the selection is used to select the first pacing output configuration including the first subset of electrodes of the multiple electrodes.

12. The cardiac therapy system of claim 11, wherein the external patient management system presents a recommendation to the user before accepting the selection.

13. The cardiac therapy system of claim 10, wherein the external patient management system accepts a selection from a user, wherein the selection is used by the controller to select the pacing output configuration including the second subset of electrodes of the multiple electrodes.

14. The cardiac therapy system of claim 1, wherein the one or more sensors comprises a heart sound sensor.

15. The cardiac therapy system of claim 1 comprising an implantable device, wherein:
   the controller is implemented by the implantable device; and
   the multiple electrodes, the one or more sensors and the pulse generator are implemented by the implantable device.

16. The cardiac therapy system of claim 1 comprising an external patient management system and an implantable device, wherein:
   the controller is at least partially implemented by the external patient management system; and
   the multiple electrodes, the one or more sensors and the pulse generator are at least partially implemented by the implantable device.

17. The cardiac therapy system of claim 16, wherein the external patient management system accepts a selection from a user, wherein the selection is used to select the first pacing output configuration including the first subset of electrodes of the multiple electrodes.

18. The cardiac therapy system of claim 17, wherein the external patient management system presents a recommendation to the user before accepting the selection.

19. The cardiac therapy system of claim 17, wherein the external patient management system presents raw data from one or more of the sensors to a user.

20. The cardiac therapy system of claim 16, wherein the external patient management system accepts a selection from a user, wherein the selection is used by the controller to select the pacing output configuration including the second subset of electrodes of the multiple electrodes.

\* \* \* \* \*